(12) United States Patent
Manera

(10) Patent No.: US 6,706,031 B2
(45) Date of Patent: Mar. 16, 2004

(54) NEEDLELESS ACCESS APPARATUS AND SYSTEM

(75) Inventor: David A. Manera, Petersburg, NJ (US)

(73) Assignee: Comar, Inc., Buena, NJ (US)

( * ) Notice: Subject to any disclaimer, the term of this patent is extended or adjusted under 35 U.S.C. 154(b) by 26 days.

(21) Appl. No.: 09/781,595

(22) Filed: Feb. 12, 2001

(65) Prior Publication Data

US 2003/0055395 A1 Mar. 20, 2003

Related U.S. Application Data

(60) Provisional application No. 60/182,628, filed on Feb. 15, 2000.

(51) Int. Cl.[7] ............................ A61M 5/32; A61M 25/16
(52) U.S. Cl. ........................ 604/411; 604/535; 604/905; 604/414
(58) Field of Search ................................ 604/411, 414, 604/415, 905, 205, 206, 412, 413, 533, 201, 534, 535, 537

(56) References Cited

U.S. PATENT DOCUMENTS 5,171,214 A * 12/1992 Kolber et al. ............... 604/82
6,253,804 B1 * 7/2001 Safabash ..................... 141/97

* cited by examiner

Primary Examiner—Michael J. Hayes
Assistant Examiner—Lina R Kontos
(74) Attorney, Agent, or Firm—Eugene E. Renz, Jr.

(57) ABSTRACT

A needleless access system adapted to be mounted on a vial comprising a generally elongated tubular housing having an interior dividing wall, flexible hooks projecting upwardly from the dividing wall which are diametrically opposed, a pair of confronting splines projecting upwardly from the interior dividing wall, a hub insert having a piercing tip normally supported in an armed position by hook elements, a series of outwardly projecting teeth which engage and are guided in the splines during axial displacement of the hub insert relative to the splined housing, and said hub insert having means for mounting a syringe assembly whereby the hub insert maybe activated axially guided by the splines so that the piercing tip engages the stopper in a vial aligned therewith.

3 Claims, 8 Drawing Sheets

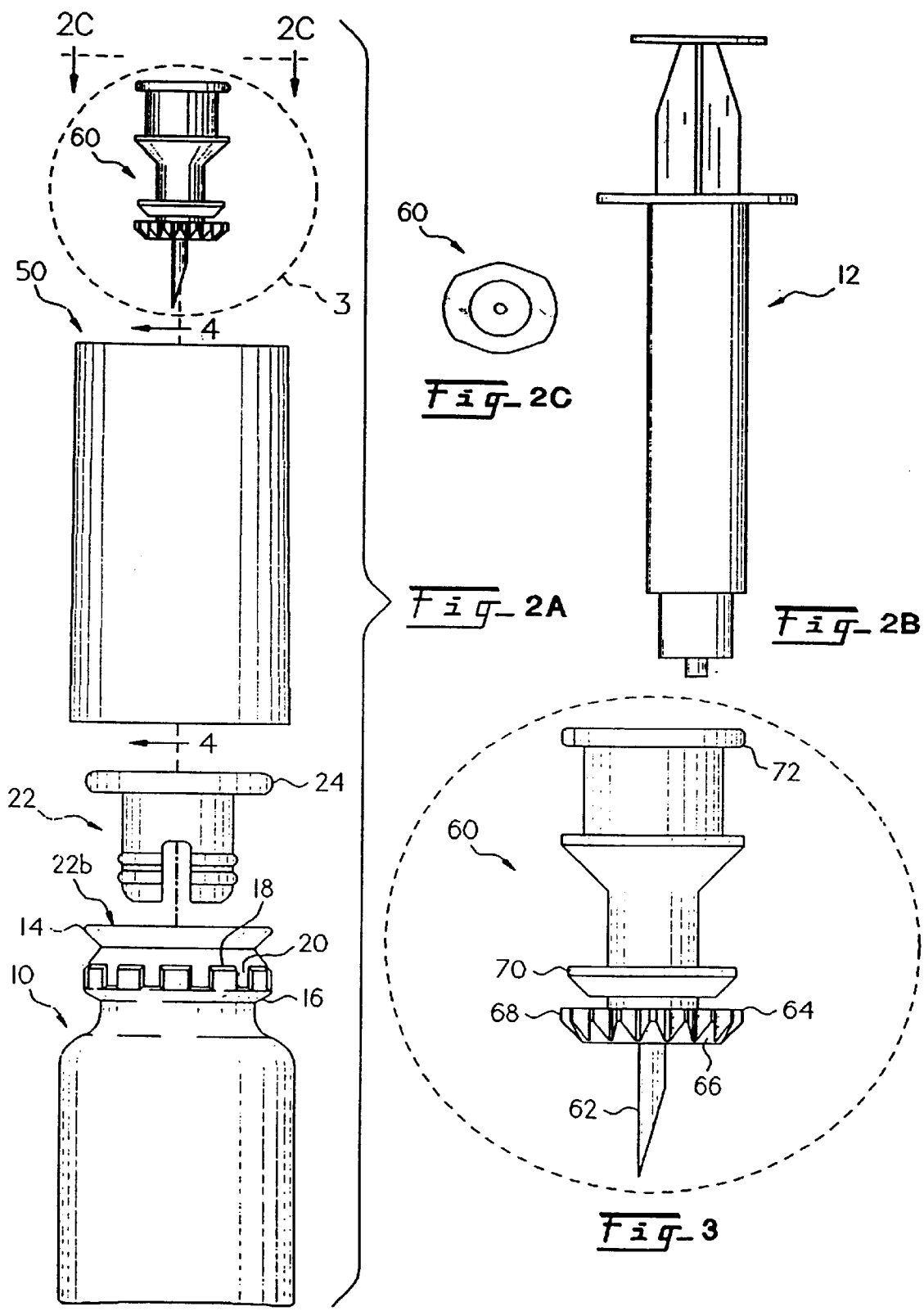

NEEDLELESS ACCESS APPARATUS AND SYSTEM

This application claims the benefit of U.S. Provisional Application No. 60/182,628 filed Feb. 15, 2000.

FIELD OF THE INVENTION

The present invention relates to needleless access systems for use in the medical field whereby medicaments can be withdrawn from vials into a syringe without exposing the user to a sharp syringe needle. More specifically, the present invention provides a novel piercing assembly for mounting on a stoppered vial and configured to receive the fitting of a syringe barrel to activate the system and withdraw the contents of the vial.

BACKGROUND OF THE INVENTION

Activation systems, generally of the type to which the present invention relates are not new per se. For example, the Aneas U.S. Pat. No. 5,879,345, issued Mar. 9, 1999 for DEVICE FOR CONNECTION WITH A CLOSED CONTAINER shows a system including a double pointed needle mounted in a sleeve overlying the stopper in one container which can be activated to transfer liquid products from one container to another.

The Weiler U.S. Pat. No. 5,718,346 for a TORQUE-RESISTANT CLOSURE WITH A LUER INSERT FOR A HERMETICALLY SEALED CONTAINER discloses container closures generally, and more specifically, to an assembly providing a torque resistant closure for a hermetically sealed containers. Specifically, the invention resides in providing a pre-formed closure insert, which in the principal embodiment is designated by the numeral (20) permanently received in the neck portion of a container and formed with a thermoplastic material wherein the insert (20) is provided with a rough surface perimeter providing increased contact area between the insert (20) and the inner surface of the container neck or throat (14) contiguous therewith. One of the embodiments, namely that shown in FIG. 12, incidentally shows an environment involving a transfer spike (124).

The Maietta et al. U.S. Pat. No. 5,482,176 for MEMBRANE PIERCING CLOSURE AND SPOUT ASSEMBLY, discloses a closure system for use particularly on cardboard packages or the like for milk and specifically, to a system for cutting an opening in such cardboard packages or cartons which functions as a pour spout. The closure pour spout assembly as shown in FIG. 4 comprises a closure cap (32), a spout member (34) and a piercing fitment (26) which inter-engage and nest in the manner shown in FIG. 4 and actuatable relative to one another between the nested position shown in FIG. 4 and an activated position wherein the piercing element creates a discharge opening in the carton to allow pouring of the contents.

Other prior art includes the patents listed below.

Kolber et al. U.S. Pat. No. 5,171,214 DRUG STORAGE AND DELIVERY SYSTEM Issued: Dec. 15, 1992

Szempruch et al. U.S. Pat. No. 5,755,712 TAMPER EVIDENCE FEATURE FOR STERILE PORT AND CAP SYSTEM Issued: May 26, 1998

Niedospial, Jr. et al. U.S. Pat. No. 5,817,082 MEDICAMENT CONTAINER CLOSURE WITH INTEGRAL SPIKE ACCESS MEANS Issued: Oct. 6, 1998

Jansen et al. U.S. Pat. No. 5,890,610 VIAL CONNECTOR ASSEMBLY FOR A MEDICAMENT CONTAINER Issued: Apr. 6, 1999

Daubert et al. U.S. Pat. No. 5,891,129 CONTAINER CAP ASSEMBLY HAVING AN ENCLOSED PENETRATOR Issued: Apr. 6, 1999

Niedospial, Jr. U.S. Pat. No. 5,895,383 MEDICAMENT CONTAINER CLOSURE WITH RECESSED INTEGRAL SPIKE ACCESS MEANS Issued: Apr. 20, 1999

Niedospial, Jr. et al. U.S. Pat. No. 5,902,298 MEDICAMENT CONTAINER STOPPER WITH INTEGRAL SPIKE ACCESS MEANS Issued: May 11, 1999

Avallone U.S. Pat. No. 5,919,182 MEDICAL FLUID TRANSFER AND DELIVERY DEVICE Issued: Jul. 6, 1999

SUMMARY OF THE INVENTION

The present invention provides an improvement over the prior art systems discussed above and is characterized by novel features of construction and arrangement facilitating easy and quick and is comprised of parts which are easy and economical to manufacture and which, when assembled, facilitating easy application of the syringe to withdraw the contents without exposing the user to risk of harm or injury from a needle puncture or the like.

BRIEF DESCRIPTION OF THE DRAWINGS

These and other objects of the present invention and various features and details of the operation and construction thereof are hereinafter more fully set forth with reference to the accompanying drawings, wherein:

FIG. 2a is an exploded side elevational view of the components;

FIG. 2b is a side elevational view of the plunger and the plunger housing;

FIG. 2c is a top view of the piercing element taken along line 2c—2c of FIG. 2a;

FIG. 3 is an enlarged side elevational view of the piercing element, shown n broken lines in FIG. 3;

DETAILED DESCRIPTION OF THE PREFERRED EMBODIMENT

Figure 1:
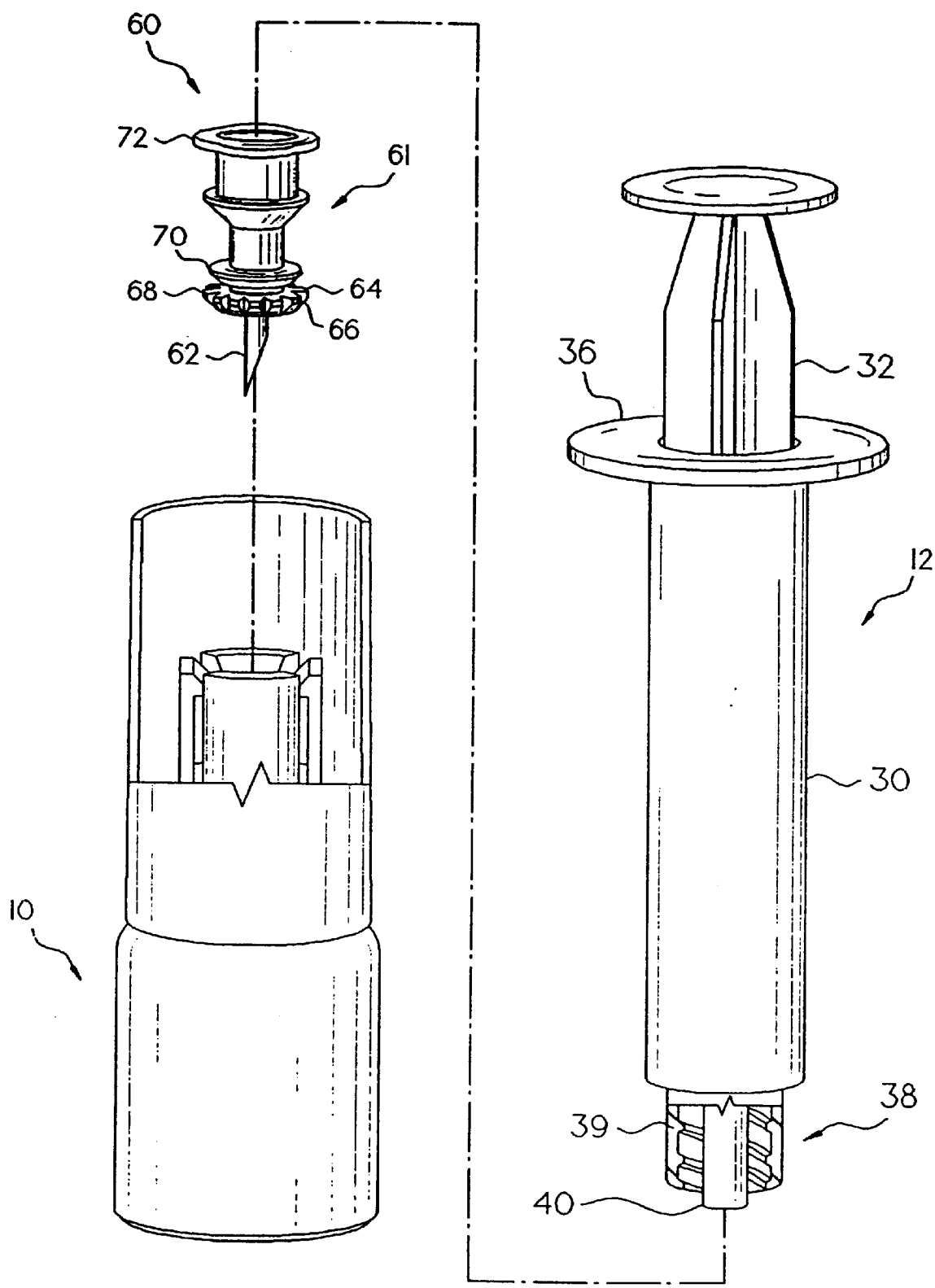
FIG. 1 is an exploded perspective view of the various components of the needleless access system of the present invention.

Referring to the drawings and, more particularly to FIGS. 1–3 thereof, there is shown a needleless access system in accordance with the present invention for withdrawing medicaments from a vial (10) into a syringe (12). The vial (10) as best illustrated in FIG. 2*a*, has a finish including an outwardly flared lip (14) at the discharge end and a buttress ring (16) below the lip, consisting of a series of circumferentially spaced, radially outwardly projecting gears (18) defining there between a plurality of circumferentially spaced recesses (20). A stopper (22) seats in the discharge opening of the vial and has a radially outwardly directed flange (24) which engages the axial end face (22*b*) of the lip (14) when it is seated in the vial in the manner shown in FIG. 8.

The syringe assembly (12) comprises an elongated generally tubular or cylindrical barrel (30), an elongated plunger rod (32) engaging interiorly of the barrel (30) mounting a plunger (34) at its end and a finger grip portion (36) at its opposite end. The discharge end of the barrel, in the present instance, is a luer lock (38) comprising an interiorly threaded sleeve (39) spaced from the discharge tip (40) of the syringe (12).

The needleless access system further includes an elongated tubular housing (50) having an interior dividing wall (52). Two diametrically opposed flexible hooks (54) project upwardly from the inner edge of the dividing wall (52). A pair of arcuate splines (56) which are likewise diametrically opposed also project from the inner edge of the dividing wall (52). The hooks (54) and splines (56) provide a mounting arrangement for a hub insert (60) as shown in FIGS. 1 and 2*a*. The hub insert (60) has a piercing element (62) at its lower end, and a gear element (64) comprising a series of circumferentially extending radially, outwardly projecting teeth (66) which engage and are guided in the splines (56) to allow for axial displacement of the hub insert (60) in the spline housing (50) and wherein the inter-engagement of the teeth (66) with the splines (56) prevents rotation of the hub insert (60). The hub insert (60) has an enlarged hub portion (61) and is defined by a series of axially spaced, radially outwardly directed circumferentially extending rings, a lower ring (68), an intermediate ring (70), and an upper ring (72).

Figure 4:
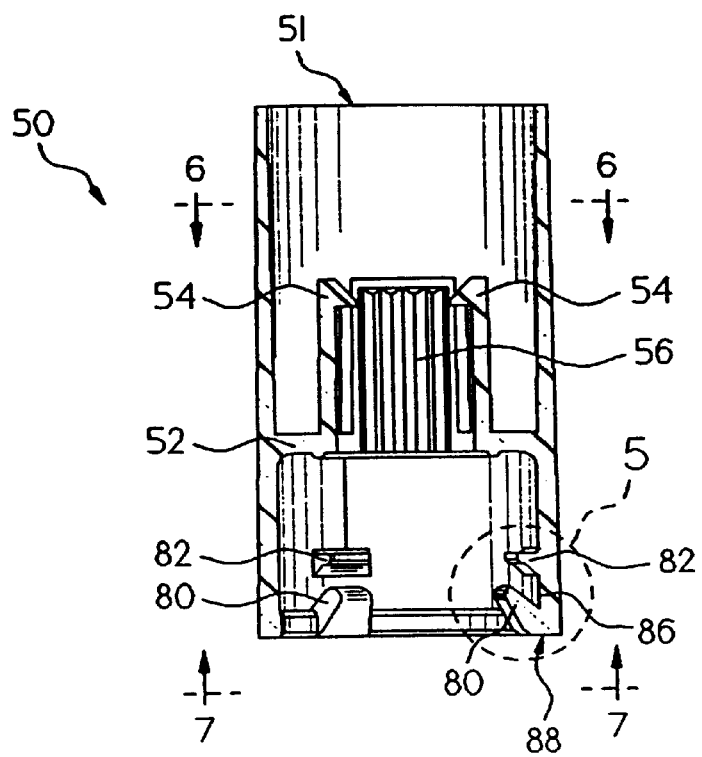
FIG. 4 is a transverse sectional view of the elongated sleeve for mounting the piercing element.
Figure 5:
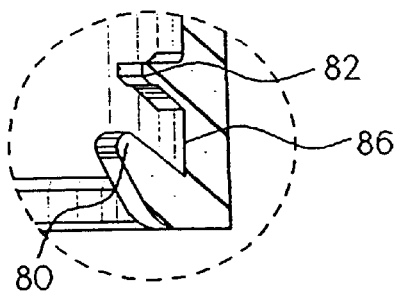
FIG. 5 is an enlarged fragmentary view of the portions circled in FIG. 4 for locking the device to the vial by way of flex-tangs.
Figure 6:
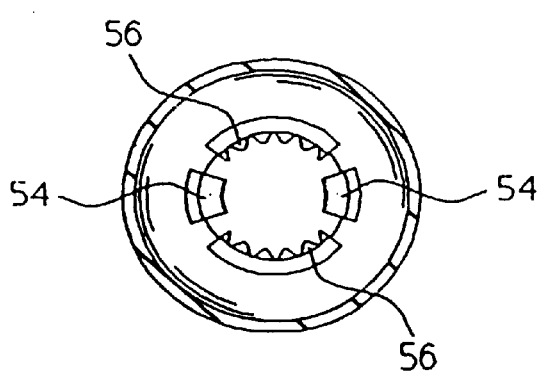
FIG. 6 is a sectional view taken on lines 6—6 of FIG. 4.
Figure 7:
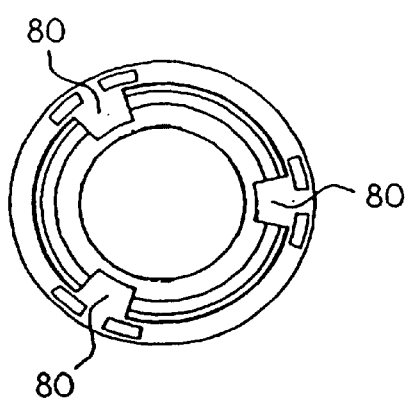
FIG. 7 is a bottom plan view of the sleeve as viewed along the lines of 7—7 of FIG. 4.

Considering now the lower portion of the main housing (50) below the dividing wall (52) has a series of circumferentially spaced tangs (80) which project radially inwardly and upwardly from the lower edge (88) of the housing, as illustrated in FIG. 4. A companion rib (82) for each of the tangs (80) projects radially inwardly and is spaced from the tang (80) to define a gap (86) between the tang (80) and the rib (82). When the housing (50) is assembled to the vial (10), the tangs (80) engage under the buttress ring (16) to firmly seat the dividing wall (52) against the diaphragm or top wall (24) of the stopper (22) and the ribs (82) engage in the spaces (20*a*) between the gear portions (20) so that the hub insert housing (50) cannot rotate relative to the vial.

Considering now operation and use of the needleless access system of the present invention. The major components of the present system, such as the hub insert (60), hub insert housing (50) and vial (10) and stopper (22) are pre-assembled in the manner shown in FIG. 8 after the vial has been filled with a medicament under aseptic conditions. The opening at the top of the housing (51) may be covered with a foil induction seal (53) that maintains the inside of the housing (50) and the hub (60) sterile prior to use, the foil (53) being removed prior to activation. Note that in this position, the hub insert (60) is seated in an unarmed position (FIG. 8) wherein the hook portions (54) of the spline housing (50) engage in the gap between the lower and intermediate rings (70) and the gear teeth (66) engage with the splines (56) to prevent rotation of the hub insert (60) in the spline housing (50).

Figure 8:
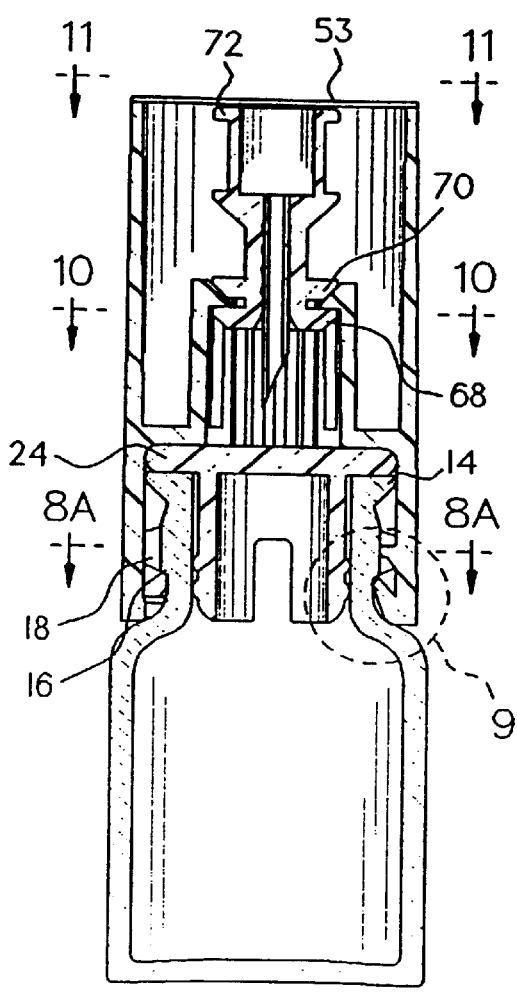
FIG. 8 is a transverse sectional view of the needleless access system of the resent invention.
Figure 8A:
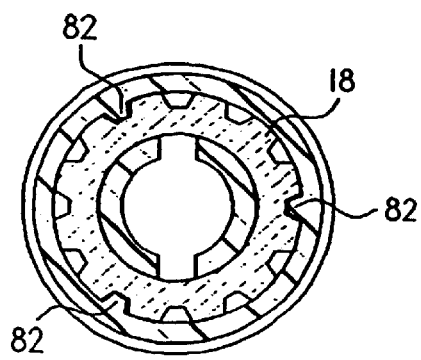
FIG. 8a is a sectional view taken on lines 8a—8a of FIG. 8.
Figure 9:
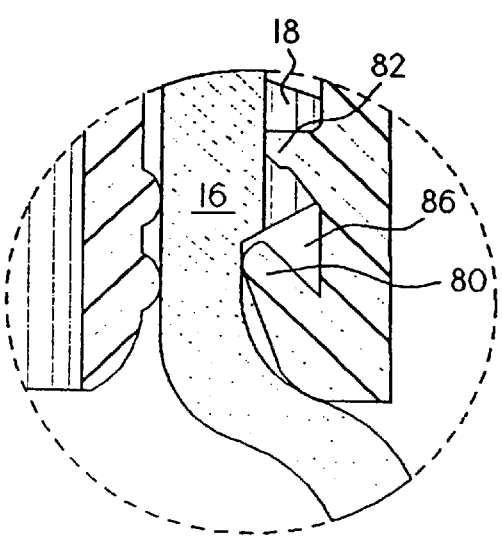
FIG. 9 is an enlarged fragmentary view showing the mounting arrangement for mounting the sleeve on the vial.
Figure 10:
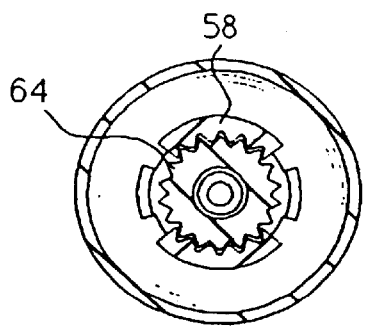
FIG. 10 is a sectional view taken along line 10—10 of FIG. 8.
Figure 11:
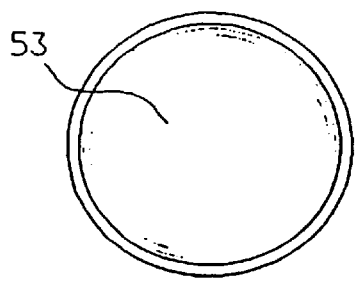
FIG. 11 is a top view of the needleless access system of the present invention taken along line 11—11 of FIG. 8.
Figure 12:
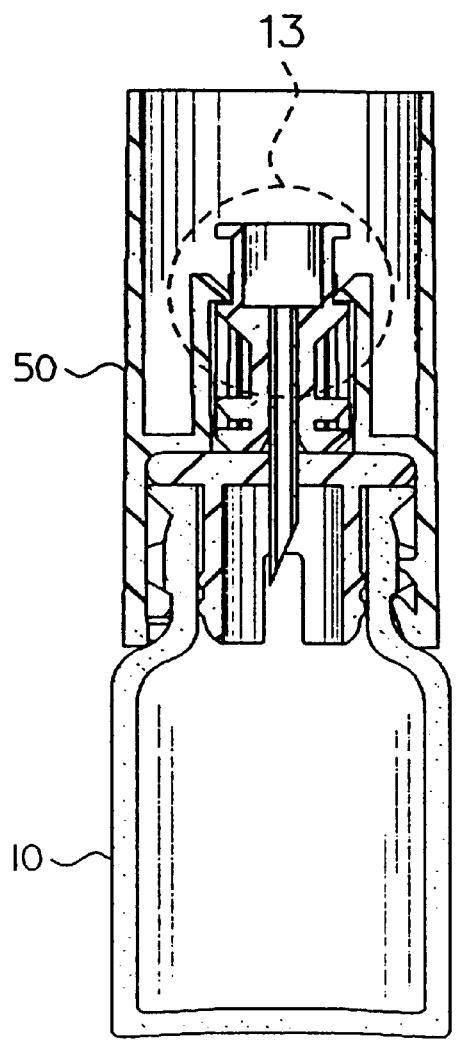
FIG. 12 is a transverse sectional view showing the piercing element in an armed position.
Figure 13:
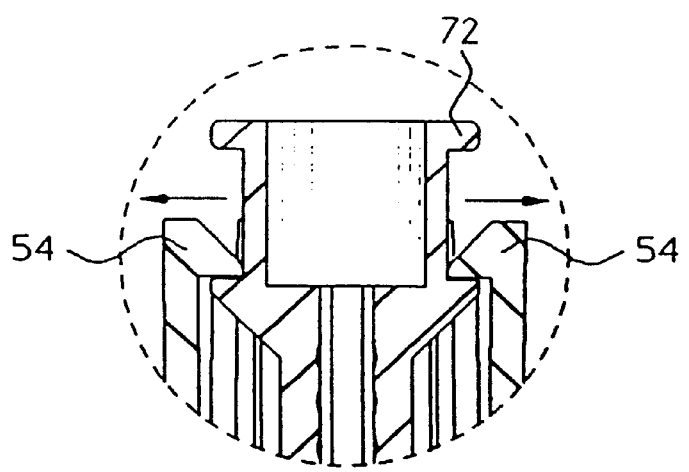
FIG. 13 is an enlarged fragmentary view of the luer lock shown in broken lines of FIG. 12.
Figure 14:
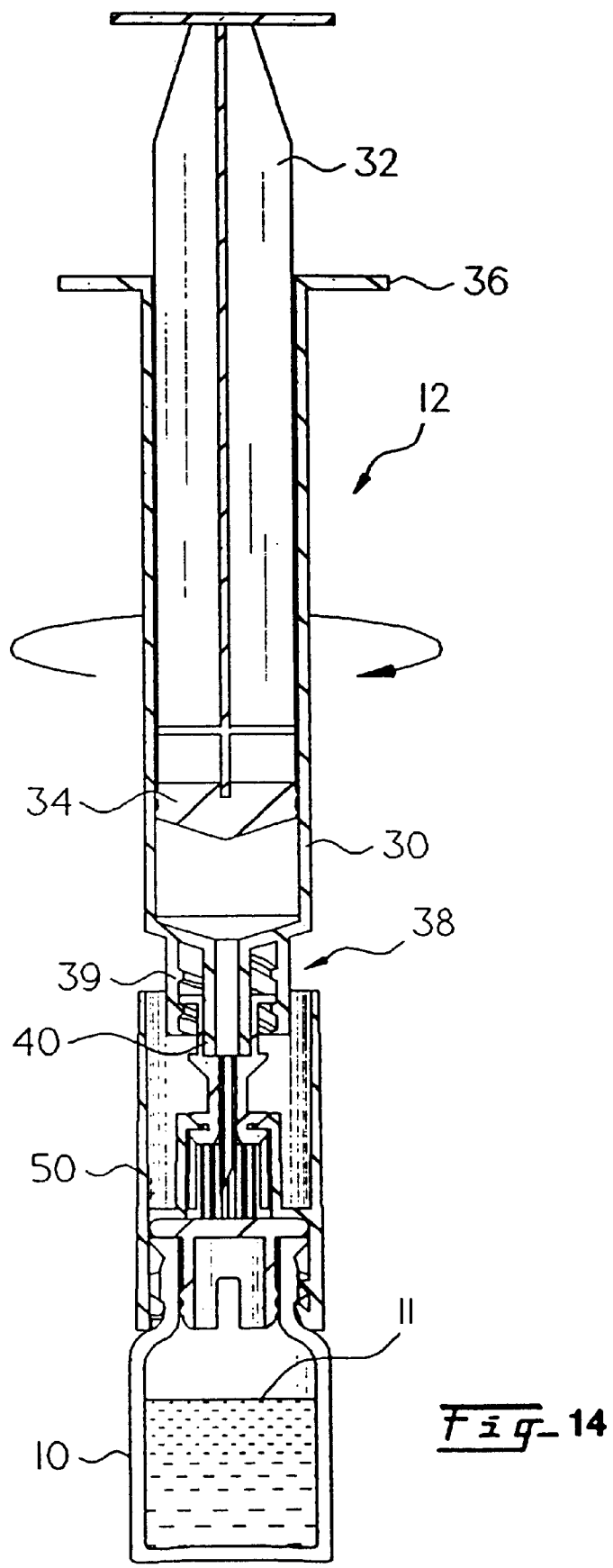
FIG. 14 is a transverse sectional view showing a syringe barrel plunger mounted on the needle hub assembly.
Figure 15:
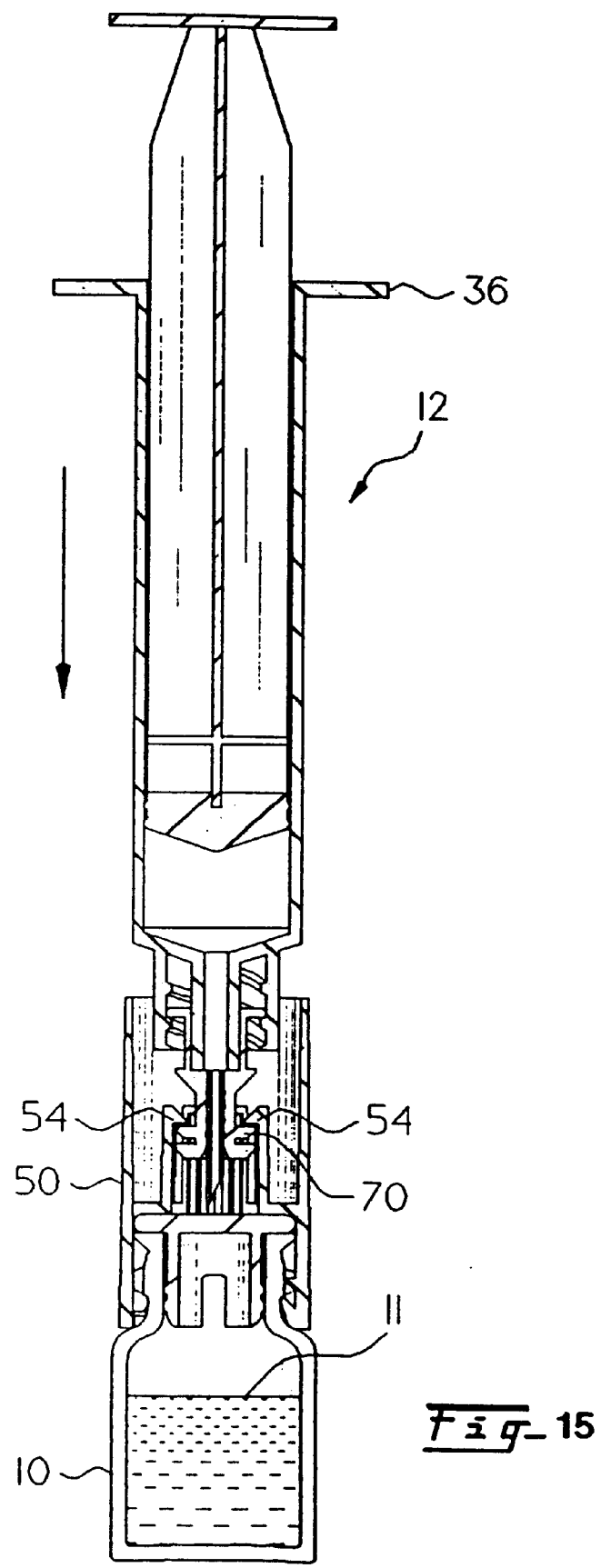
FIG. 15 is a view similar to FIG. 14, showing the parts about to be activated.
Figure 16:
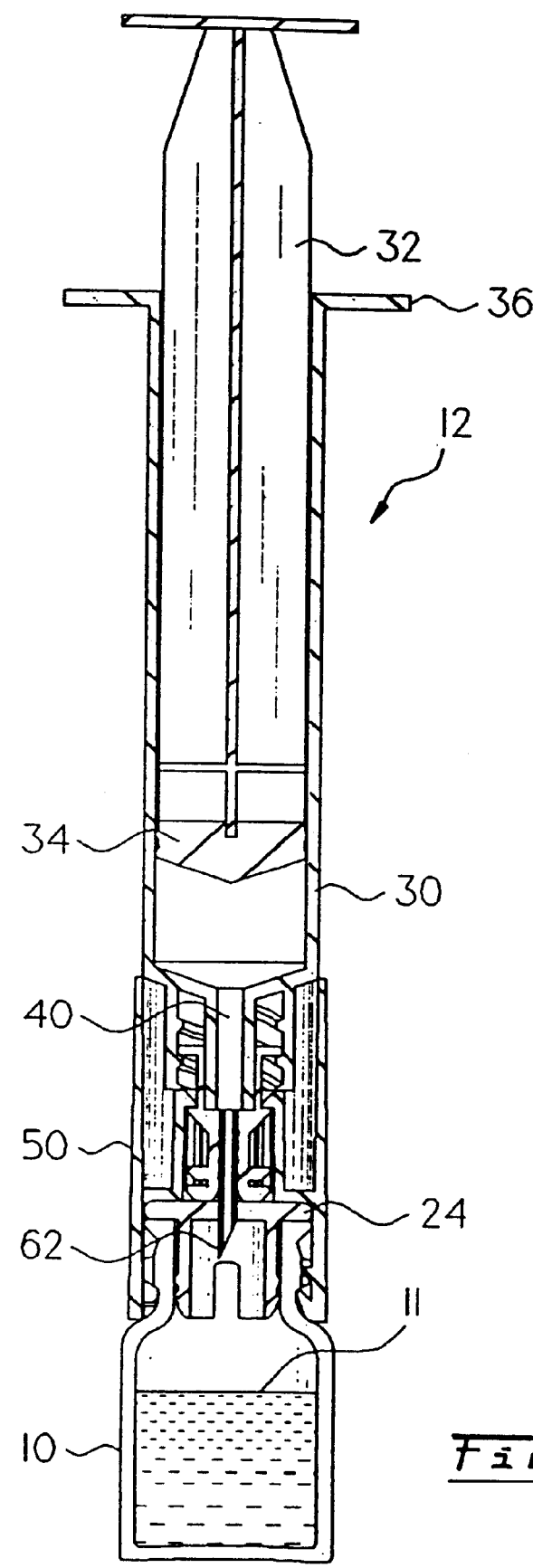
FIG. 16 is a view showing the syringe needle piercing the stopper diaphragm so that the contents of the vial may be withdrawn into the syringe barrel.

Now when the doctor or nurse wants to withdraw the medicament content from the vial, the system is activated by removing the foil induction seal (53) from the top of the housing (51) (see FIG. 8). This exposes the hub insert (60) and the syringe (12) can be assembled simply by turning the threaded portion of the syringe over the upper ring (72) of the hub to lock the components together in the manner shown in FIG. 14. The syringe (12), then, can be pushed downwardly in the direction of the arrows as shown in FIG. 15 which releases the hub insert (60) from the hooks (54) until the piercing element (62) passes through the diaphragm (24) in the manner shown in FIG. 16. The nurse or doctor can then draw the syringe plunger (34) upwardly to evacuate the medicament (11) from the vial (10) and fill the syringe (12). When completed, the syringe (12) is simply rotated to release it from the hub insert (60). The housing (50), hub insert (60), and vial (10) do then comprise a disposable one-time unit.

The needleless access system component of the present invention holds compression on the stopper flange (24) or optional liner to maintain container/closure integrity. The compression is achieved by snapping the three flexible tangs (80) under the buttress ring (16) of the vial (10). There are also three horizontal ribs (82) that engage the gear portion of the vial (10). These ribs serve the purposes of holding the optional liner in position until placed on the vial, and they also hinder rotation of the hub-housing relative to the vial. In the upper portion of the hub-housing (50) there are two flexible hooks 180 degrees apart, which are arranged around an internal spline (56). The hooks (54) are used to hold the hub (60) between the lower (68) and intermediate rings (70) and maintain the hub (60) in this position until activated. They also lock the hub (60) in the down or activated position by locking above the upper ring (72) on the hub once the spike pierces the rubber component. The internal spline (56) of the hub-housing (50) is used to engage the front gear diameter of the hub to eliminate rotation of the hub relative to the hub housing. The stopper finish gear vial is number 6. This needleless access system component has a combination gear and buttress ring (16). The buttress ring (16) is used as a locking feature for the flexible tangs (80) to lock below while the gear portion (18) is used to engage the horizontal ribs (82) of the hub-housing (50) to hinder rotation. The top of the vial (10) was designed with a special lip (14) to eliminate the pinching of the stopper flange (24) that occurred when placing the hub-housing over a standard gear finish vial (10). The special lip (14) allows the flange (24) to bend around and under the lip (14) causing the flange (24) to stretch thinner which allows the flexible tangs (80) and horizontal ribs (82) to pass by without pinching the flange (24).

The Harmony needleless access system of the present invention is designed to eliminate accidental needle sticks by doctors and nurses. This is possible because the drug can be removed from the vial using a standard syringe without attaching a needle to it first.

The hub (60) will be assembled into the housing (50) in the up position or pre-activated position. The opening on the top (51) of the housing will be covered with a foil induction seal (53) that will keep the inside of the housing (50) and the hub (60) sterile prior to use. The foil (53) will be removed prior to activation. The drug companies will assemble the housing/hub assembly post filling and stoppering of the vials. Step 1: The doctor/nurse will activate the system by removing the foil induction seal from the top of the housing. Step 2: A standard luer lock syringe will be attached to the hub by turning the threaded portion of the syringe over the radial flanges of the hub, therefore locking the two components together (see page 3). Step 4: The syringe (12) will then be pushed forward to activate the system and locking the hub (60) onto the down or activated position (see page 4). The syringe (12) is then unlocked from the hub (60) by rotating in the counterclockwise direction and the contents can now be administered to the patient.

Even though particular embodiments of the present invention have been illustrated and described herein, it is not intended to limit the invention and changes and modifications may be made therein within the scope of the following claims.

What is claimed is:

1. A needleless access system adapted to be mounted on a vial comprising:

a generally elongated tubular housing having an interior dividing wall, flexible hooks projecting upwardly from the dividing wall which are diametrically opposed;

a pair of confronting splines projecting upwardly from the interior dividing wall;

a hub insert having a piercing tip normally supported in an armed position by hook elements;

a series of outwardly projecting teeth which engage and are guided in the splines during axial displacement of the hub insert relative to the splined housing; and said hub insert having means for mounting a syringe assembly whereby the hub insert maybe activated axially guided by the splines so that the piercing tip engages the stopper in a vial aligned therewith.

2. A system as claimed in claim 1 wherein said insert has a pair of axially spaced, radially outwardly projecting flanges which engage the flexible hooks in the unarmed position of the hub insert and are releasable therefrom when the hub insert is actuated axially to an armed position.

3. A system as claimed in claim 1 wherein said main housing has a series of circumferentially spaced, radially inwardly and upwardly extending tangs and a series of companion ribs spaced from the tangs to define a gap which engage under a buttress ring on the neck of a container to firmly seat the dividing wall against a stopper in the container and wherein the ribs engage in the spaces between the gear portions of the buttress ring to prevent rotation of the said housing relative to the vial.

* * * * *